(12) United States Patent
Malenchek

(10) Patent No.: US 6,926,697 B2
(45) Date of Patent: Aug. 9, 2005

(54) ADAPTOR FOR CONVERTING A NON-SAFETY SYRINGE INTO A SAFETY SYRINGE

(76) Inventor: Robert Malenchek, 279 Sunnymead Rd., Hillsborough, NJ (US) 08844

( * ) Notice: Subject to any disclaimer, the term of this patent is extended or adjusted under 35 U.S.C. 154(b) by 48 days.

(21) Appl. No.: 10/437,424

(22) Filed: May 13, 2003

(65) Prior Publication Data

US 2004/0230158 A1 Nov. 18, 2004

(51) Int. Cl.[7] .............................................. A61M 5/32
(52) U.S. Cl. ...................................... 604/197; 604/198
(58) Field of Search ......................... 604/110, 164.08, 604/187, 192, 197, 198; 128/919

(56) References Cited

U.S. PATENT DOCUMENTS

| | | |
|---|---|---|
| 4,699,614 A | 10/1987 | Glazier |
| 4,801,295 A | 1/1989 | Spencer |
| 4,850,968 A | 7/1989 | Romano |
| 4,850,977 A | 7/1989 | Bayless |
| 4,883,466 A | 11/1989 | Glazier |
| 4,900,311 A | 2/1990 | Stern et al. |
| 4,911,693 A | 3/1990 | Paris |
| 4,927,416 A | 5/1990 | Tomkiel |
| 4,929,237 A | 5/1990 | Medway |
| 4,932,940 A | 6/1990 | Walker et al. |
| 4,932,947 A | 6/1990 | Cardwell |
| 4,946,446 A | 8/1990 | Vadher |
| 4,955,868 A | 9/1990 | Klein |
| 4,966,592 A | 10/1990 | Burns et al. |
| 4,973,316 A | 11/1990 | Dysarz |
| 4,978,343 A | 12/1990 | Dysarz et al. |
| 5,013,301 A | 5/1991 | Marotta, Jr. et al. |
| 5,019,051 A | 5/1991 | Hake |
| 5,026,354 A | 6/1991 | Kocses |
| 5,049,133 A | 9/1991 | Villen Pascual |
| 5,049,136 A | 9/1991 | Johnson |
| 5,053,018 A | 10/1991 | Talonn et al. |
| 5,057,079 A | 10/1991 | Tiemann et al. |
| 5,066,277 A | 11/1991 | Carrell et al. |
| 5,088,986 A | 2/1992 | Nusbaum |
| 5,088,988 A | 2/1992 | Talonn et al. |
| 5,112,307 A | 5/1992 | Haber et al. |
| 5,127,910 A | 7/1992 | Talonn et al. |
| 5,147,303 A | 9/1992 | Martin |
| 5,147,326 A | 9/1992 | Talonn et al. |
| 5,160,326 A | 11/1992 | Talonn et al. |
| 5,180,370 A | 1/1993 | Gillespie |
| 5,273,541 A | 12/1993 | Malenchek |
| 5,279,584 A | 1/1994 | Dillard, III et al. |
| 5,312,347 A | 5/1994 | Osborne et al. |
| 5,312,370 A | 5/1994 | Talonn et al. |
| 5,314,414 A | 5/1994 | Hake et al. |
| 5,318,538 A | 6/1994 | Martin |

(Continued)

FOREIGN PATENT DOCUMENTS

| | | |
|---|---|---|
| EP | 0 506 204 A2 | 9/1992 |
| GB | 2 243 552 A | 11/1991 |
| GB | 2 283 683 A | 5/1995 |
| WO | WO 90/06148 | 6/1990 |
| WO | WO 93/25254 | 12/1993 |
| WO | WO 99/32177 A1 | 7/1999 |

Primary Examiner—Nicholas D. Lucchesi
Assistant Examiner—Catherine S. Williams
(74) Attorney, Agent, or Firm—McCarter & English, LLP

(57) ABSTRACT

A safety syringe is provided which includes a shield and a barrel mounted for reciprocating movement within the shield. The safety syringe includes a hub sized and shaped so as to be attached to the barrel and a ring rotatably mounted to the hub. The ring includes a tab that cooperates with the grooves in the interior wall of the shield for locking the barrel within the shield so as to allow for a single use of the safety syringe.

20 Claims, 9 Drawing Sheets

U.S. PATENT DOCUMENTS

| | | |
|---|---|---|
| 5,338,304 A | 8/1994 | Adams |
| 5,338,311 A | 8/1994 | Mahurkar |
| 5,346,480 A | 9/1994 | Hess et al. |
| 5,383,863 A | 1/1995 | Mardones |
| 5,389,085 A | 2/1995 | D'Alessio et al. |
| 5,403,286 A | 4/1995 | Lockwood, Jr. |
| 5,403,287 A | 4/1995 | Talonn et al. |
| 5,411,487 A | 5/1995 | Castagna |
| 5,415,645 A | 5/1995 | Friend et al. |
| 5,417,660 A | 5/1995 | Martin |
| 5,429,612 A | 7/1995 | Berthier |
| 5,429,613 A | 7/1995 | D'Amico |
| 5,433,712 A | 7/1995 | Stiles et al. |
| 5,437,639 A | 8/1995 | Malenchek |
| 5,445,620 A | 8/1995 | Haber et al. |
| 5,472,430 A | 12/1995 | Vaillancourt et al. |
| 5,478,314 A | 12/1995 | Malenchek |
| 5,484,421 A | 1/1996 | Smocer |
| 5,492,536 A | 2/1996 | Mascia |
| 5,498,243 A | 3/1996 | Vallelunga et al. |
| 5,512,050 A | 4/1996 | Caizza et al. |
| 5,549,558 A | 8/1996 | Martin |
| 5,554,122 A | 9/1996 | Emanuel |
| 5,554,130 A | 9/1996 | McDonald et al. |
| 5,562,626 A | 10/1996 | Sanpietro |
| 5,573,513 A | 11/1996 | Wozencroft |
| 5,591,138 A | 1/1997 | Vaillancourt |
| 5,634,903 A | 6/1997 | Kurose et al. |
| 5,643,222 A | 7/1997 | Mahurkar |
| 5,647,849 A | 7/1997 | Kalin |
| 5,688,241 A | 11/1997 | Asbaghi |
| 5,713,873 A | 2/1998 | Jehle |
| 5,735,823 A | 4/1998 | Berger |
| 5,779,683 A | 7/1998 | Meyer |
| 5,843,041 A | 12/1998 | Hake et al. |
| 5,980,494 A | 11/1999 | Malenchek et al. |
| 5,984,899 A | 11/1999 | D'Alessio et al. |
| 6,015,396 A | 1/2000 | Buttgen et al. |
| 6,083,199 A | 7/2000 | Thorley et al. |
| 6,183,446 B1 | 2/2001 | Jeanbourquin |
| 6,206,853 B1 | 3/2001 | Bonnet |
| 6,475,194 B2 | 11/2002 | Domici, Jr. et al. |
| 6,527,742 B1 * | 3/2003 | Malenchek ............... 604/110 |
| 2001/0037088 A1 * | 11/2001 | Domici et al. ............ 604/187 |

* cited by examiner

ADAPTOR FOR CONVERTING A NON-SAFETY SYRINGE INTO A SAFETY SYRINGE

FIELD OF THE INVENTION

The present invention relates to syringes, and, more particularly, to an adaptor assembly that converts a conventional non-safety syringe into a safety syringe.

BACKGROUND OF THE INVENTION

Syringes are commonly used for hypodermic injection. In general, a conventional syringe includes a barrel which has a cavity for storing a desired fluid, a needle assembly which includes a needle and which is secured to the barrel, and a plunger rod which is selectively inserted or removed from the cavity.

Conventional syringes have various shortcomings and disadvantages. For example, a needle prick injury is a common problem suffered by users (e.g., medical practitioners) of conventional syringes. In order to prevent needle prick injuries, safety syringes have been developed. These safety syringes typically include a shield which secures the needle therein. A locking mechanism may also be included which allows the needle to be temporarily secured in the shield prior to use of the safety syringe and to be permanently locked therein after use of the safety syringe, thereby preventing further use of the safety syringe and preventing needle pricks.

Some of these safety syringes, however, require complicated designs which result in increased manufacturing, distribution, and stocking costs. Because of such costs, it may not be feasible to replace conventional non-safety syringes with safety syringes. Accordingly, there is a need to convert conventional non-safety syringes into safety syringes in a relatively inexpensive manner.

SUMMARY OF THE INVENTION

The present invention relates to a new and improved safety syringe that overcomes the disadvantages and shortcomings of the prior art discussed above. More particularly, the new and improved safety syringe of the present invention includes a shield and a spring-biased barrel mounted for reciprocating movement within the shield, as well as a hub which is sized and shaped so as to be attached to the barrel. A ring, which is rotatably mounted to the hub, includes a tab that cooperates with grooves in the interior wall of the shield for locking the barrel within the shield, thereby allowing for a single use of the safety syringe and preventing needle pricks. The shield, hub, spring, and ring are components of an adaptor assembly that can be provided as original equipment or retrofitted to the barrel of a conventional non-safety syringe.

Other features and aspects of the present invention will become more fully apparent from the following detailed description of an exemplary embodiment, the appended claims and the accompanying drawings.

BRIEF DESCRIPTION OF THE DRAWINGS

For a more complete understanding of the present invention, reference is made to the following detailed description of an exemplary embodiment considered in conjunction with the accompanying drawings, in which.

DETAILED DESCRIPTION OF THE EXEMPLARY EMBODIMENT

Figure 1:
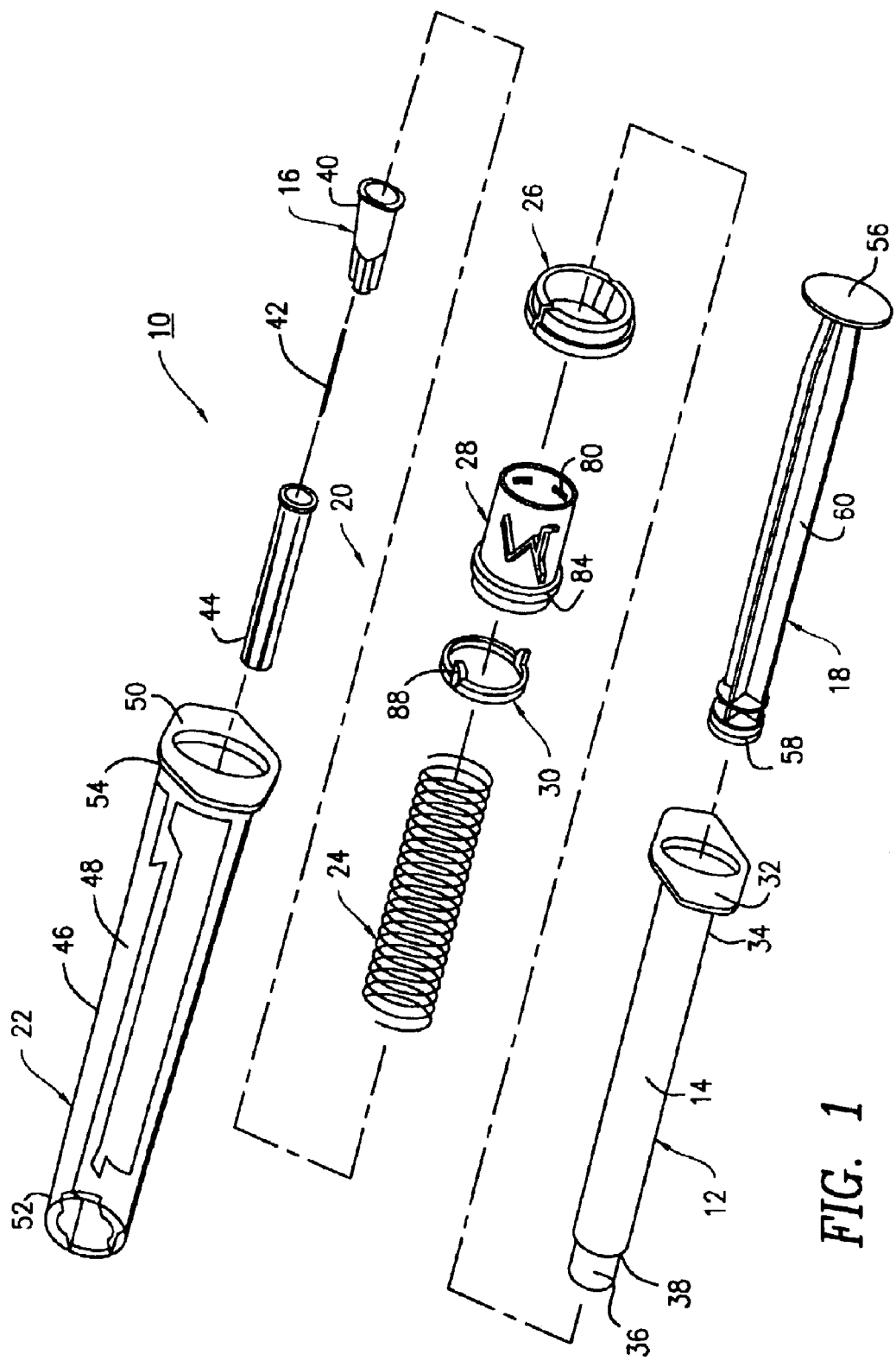
FIG. 1 is an exploded, perspective view of a safety syringe constructed in accordance with the present invention.

FIG. 1 illustrates a safety syringe 10 which includes a barrel 12 having a cavity 14 for storing a desired fluid (e.g., insulin). The safety syringe 10 also includes a needle assembly 16 releaseably secured to the barrel 12 and a plunger 18, which is selectively inserted into and removed from the cavity 14 of the barrel 12. In order to facilitate consideration and discussion, it is noted that the barrel 12, the needle assembly 16, and the plunger 18 are parts of a conventional non-safety syringe.

In order to overcome the disadvantages (e.g., needle prick injuries) associated with the use of a conventional non-safety syringe, the safety syringe 10 is further provided with an adaptor assembly 20 which includes a shield 22 sized and shaped so as to be coaxially received over the needle assembly 16, a helical compression spring 24 mounted within the shield 22, and a retaining bushing 26 mounted to the shield 22. The adaptor assembly 20 further includes an adaptor hub 28 sized and shaped such that it can be applied (i.e., retrofitted) onto the barrel 12 and a ring 30 rotatably mounted to the adaptor hub 28.

With reference to FIG. 1, the barrel 12 includes a flange 32 located on a proximal end 34 thereof, and a mounting surface 36 located on a distal end 38 thereof. The needle assembly 16 includes a needle support 40 connected to the barrel 12, a needle 42 attached to the needle support 40, and a cover 44 for the needle 42.

Still referring to FIG. 1, the shield 22 is utilized for temporarily securing the needle 42 of the needle assembly 16 therein. More particularly, the shield 22 has a cylindrical body 46 with a bore 48, as well as a finger gripping flange 50. The bore 48 extends from a distal end 52 of the shield 22 to a proximal end 54 of the shield 22. The shield 22 can be made by any suitable material such as polypropylene.

Figure 4:
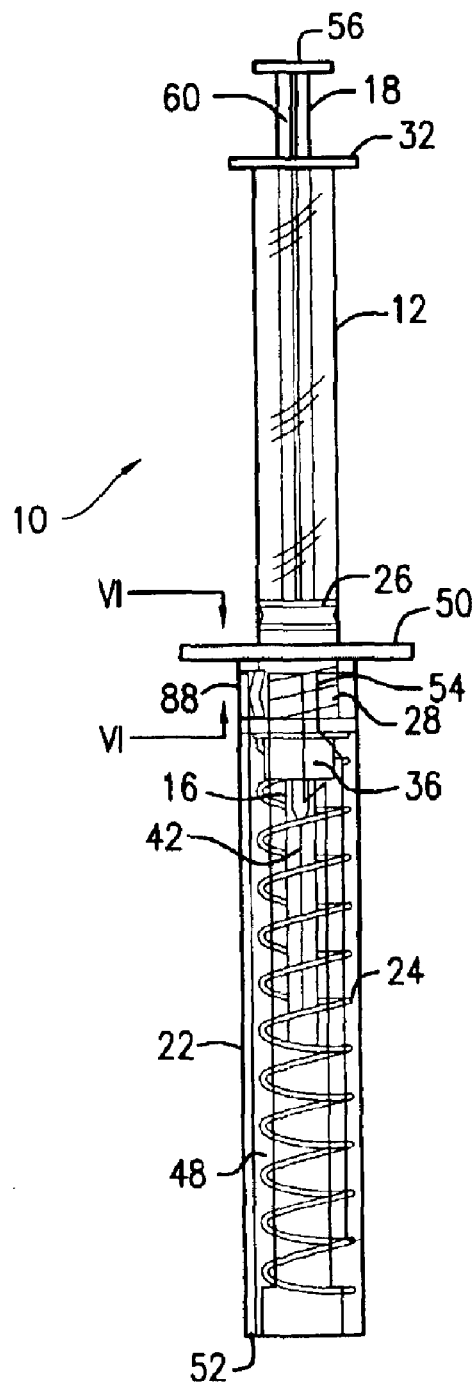
FIG. 4 is an elevational view of the safety syringe illustrated in FIG. 1, the safety syringe being shown with its barrel in a retracted position.
Figure 5:
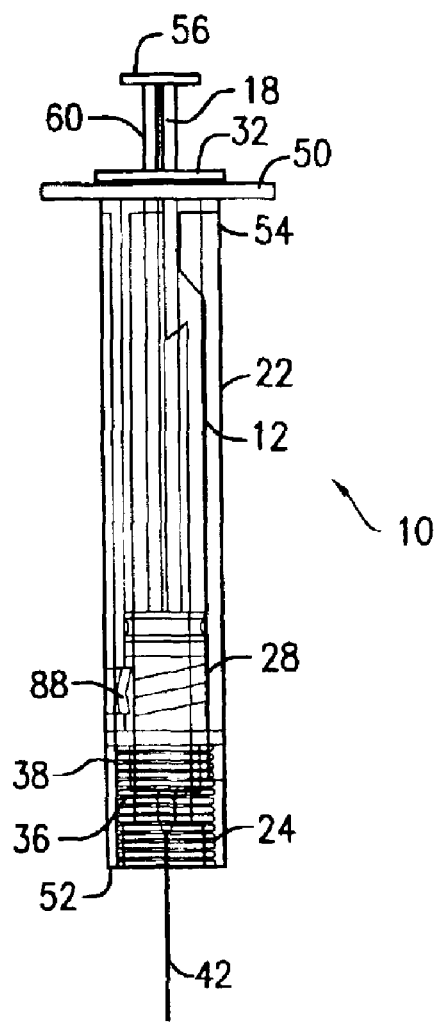
FIG. 5 is an elevational view similar to that of FIG. 4, except that the barrel of the safety syringe is shown in its extended position.

With reference to FIGS. 4 and 5, the barrel 12 is mounted for reciprocating movement within the shield 22 so as to be movable between a retracted position (see FIG. 4), in which position the needle 42 retracts into and is secured within the shield 22, and an extended position (see FIG. 5), in which position the needle 42 extends from the shield 22. As illustrated in FIGS. 4 and 5, the mounting surface 36 (i.e., the distal end 38) of the barrel 12 is located adjacent to the proximal end 54 of the shield 22 when the barrel 12 is in its retracted position, and is located adjacent to the distal end 52 of the shield 22 when the barrel 12 is in its extended position.

Referring to FIG. 1, the plunger 18 includes a finger gripping flange 56 on one end, a sealing flange 58 on an opposite end, and a shaft 60 which connects the flanges 56, 58. The sealing flange 58 is sized and shaped so as to prevent leakage of fluid from the cavity 14 of the barrel 12. As will be described in greater detail hereinafter, the plunger 18 is mounted for reciprocating movement within the barrel 12 so as to move the barrel 12 to its extended position (see FIG. 5) when the flange 56 of the plunger 18 is pushed axially toward the shield 22.

Still referring to FIG. 1, the helical compression spring 24 is mounted within the bore 48 of the shield 22. The spring 24 extends between the flange 50 of the shield 22 and the distal end 52 of the shield 22. The spring 24 is sized and shaped so as to axially urge the barrel 12 to its retracted position (see FIG. 4), in which position the spring 24 is expanded. When the barrel 12 is in its extended position (see FIG. 5), the spring 24 is compressed. The spring 24 is designed to generate axial tension force, as well as rotational tension force.

With reference to FIG. 1, the retaining bushing 26 is sized and shaped so as to prevent removal of the syringe components during use of the safety syringe 10 (see FIG. 4). The retaining bushing 26 can be made by any suitable material such as polypropylene.

Figure 2:
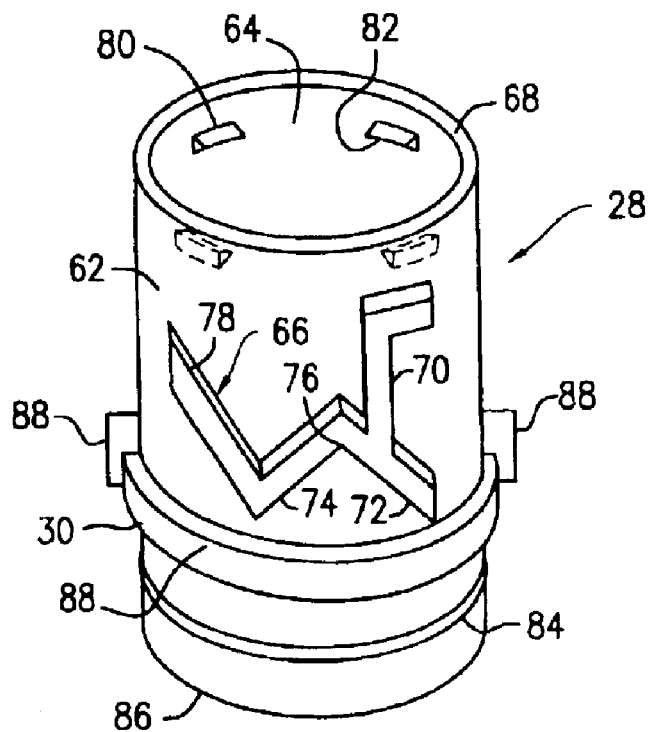
FIG. 2 is a perspective view of an adaptor assembly utilized to make the safety syringe depicted in FIG. 1.
Figure 3:
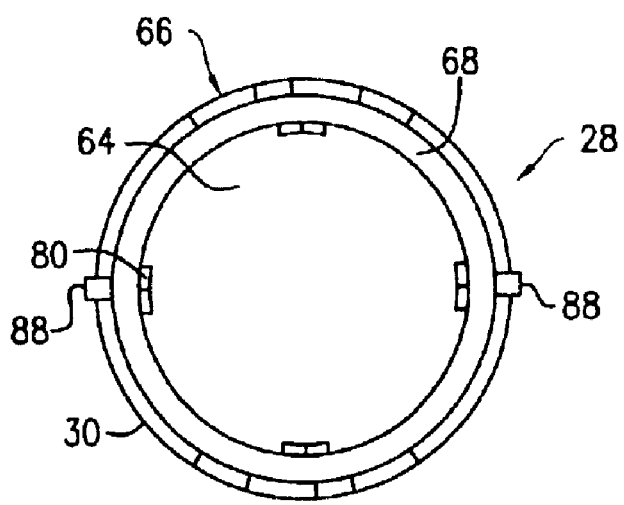
FIG. 3 is a top view of the adaptor assembly illustrated in FIG. 2.
Figure 6:
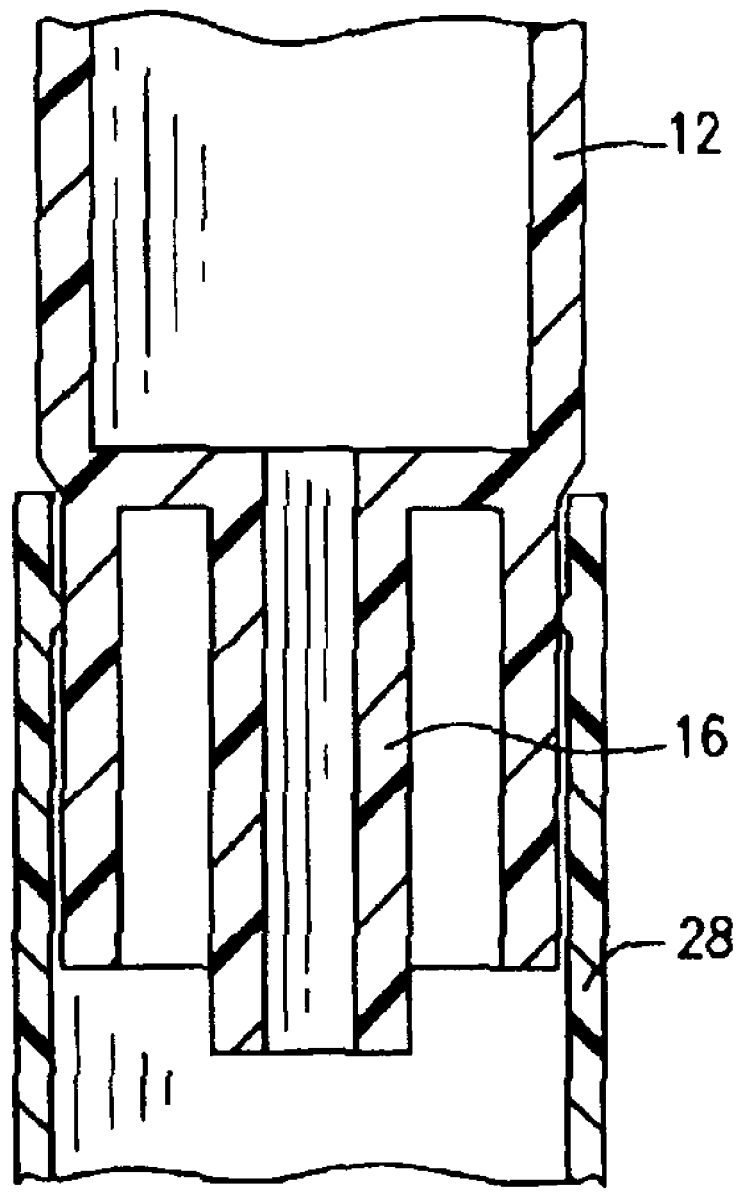
FIG. 6 is a partial cross-sectional view, taken along section line VI—VI and looking in the direction of the arrows, of the safety syringe shown in FIG. 4.

Referring to FIGS. 2 and 3, the adaptor hub 28 is sized and shaped so as to be retrofitted to the mounting surface 36 of the barrel 12 (see FIG. 6). The adaptor hub 28 includes a cylindrical wall 62 and an interior hollow 64. A pair of projections 66 (only one of which is illustrated in FIG. 2) is provided adjacent to a proximal end 68 of the adaptor hub 28. Each of the projections 66 includes an axially extending edge 70 and a first inclined ramp 72 connected to the edge 70. An angled surface 74, which functions as a stop, is connected to the first inclined ramp 72 so as to form a V-shaped trough 76. A second inclined ramp 78 is connected to the angled surface 74. The adaptor hub 28 also includes four locking barbs 80 that are connected to the wall 62 and project into the interior hollow 64. The locking barbs 80 are utilized to retain the adaptor hub 28 on the mounting surface 36 of the barrel 12. Each of the locking barbs 80 includes an edge 82 that is deformed radially outwardly relative to the wall 62 and that can move toward the wall 62 of the adaptor hub 28 during assembly of the adaptor hub 28 onto the barrel 12. Also, the adaptor hub 28 can be made of any suitable material such as polyproplyene.

Still referring to FIG. 2, the adaptor hub 28 includes a cylindrical retention bead 84 positioned adjacent to a distal end 86 thereof. The retention bead 84 projects radially outwardly from the wall 62 of the adaptor hub 28 and is utilized for purposes to be described hereinafter.

Still referring to FIG. 2, the cylindrical ring 30 is provided with a pair of external tabs 88 (which are schematically illustrated in FIGS. 8–16 as "TAB 1" and "TAB 2", respectively). The two tabs 88 are circumferentially spaced so as to be diametrically opposed around the exterior of the ring 30. The ring 30 is sized and shaped so as to be rotatably mounted to the wall 62 of the adaptor hub 28 such that the tabs 88 can rotate about the wall 62 and can be axially displaced along the wall 62. As will be described in greater detail hereinafter, the tabs 88 are sized and shaped so as to position the ring 30 in various positions relative to the adaptor hub 28. The ring 30 can be made by a material such as polypropylene. The retention bead 84 functions to retain the ring 30 on the adaptor hub 28. In this manner, the ring 30 is captured between the projections 66 and the retention bead 84.

Figure 7:
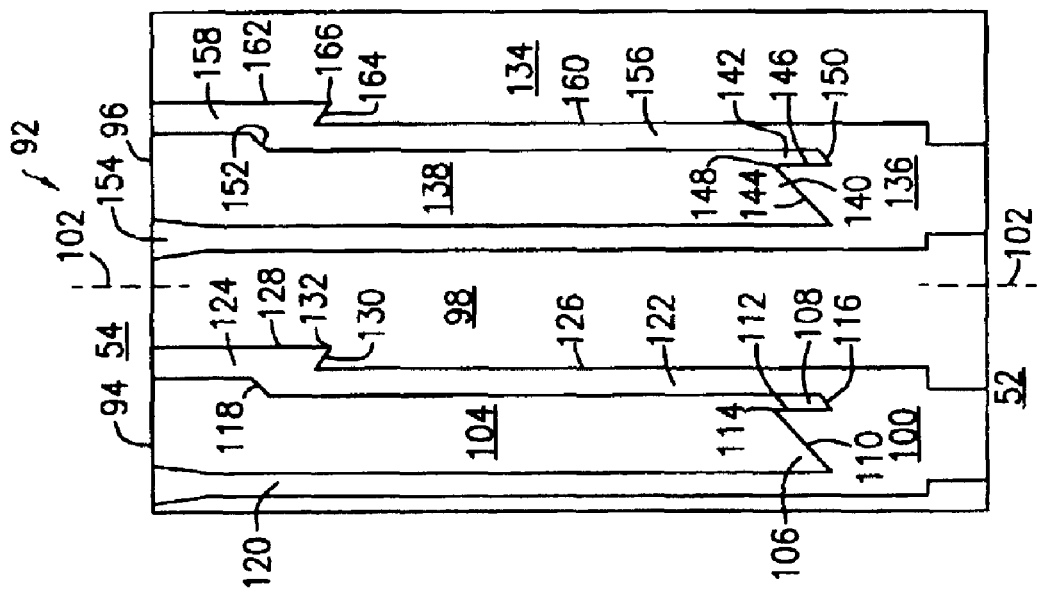
FIG. 7 is a fragmentary flattened view of an interior of a shield used in the safety syringe illustrated in FIG. 4.

Referring to FIG. 7, an interior wall 92 of the shield 22 is illustrated in a flattened position. The interior wall 92 of the shield 22 includes two sets 94, 96 of the following features. The first set 94 includes an elevated segment 98 and an open area 100, each of which extends along a longitudinal axis 102 and is circumferentially spaced from the other. The open area 100 includes a raised segment 104 having a distal edge in the form of ratchet teeth 106, 108. More particularly, the tooth 106 has an inclined edge 110 which functions as a ramp so as to allow "TAB 1" (see FIG. 9) to slide therealong. The other tooth 108 has an axially extending linear edge 112 which functions as a stop, positioned adjacent to the inclined edge 110 so as to form a V-shaped trough 114 between the ratchet teeth 106, 108. The V-shaped trough 114 is sized and shaped so as to temporarily lock "TAB 1" (see FIG. 10) of the ring 30 therein as will be explained in further detail hereinafter.

Both the inclined edge 110 and the linear edge 112 of the ratchet teeth 106, 108 protrude into the open area 100 and are located adjacent to the distal end 52 of the shield 22. The tooth 108 also includes a lower lock ramp 116 which functions as a glide and which is positioned adjacent the linear edge 112 of the ratchet tooth 108. The raised segment 104 has a proximal edge in the form of an upper lock ramp 118.

A linearly extending assembly groove 120 is formed on one side of the raised segment 104. The assembly groove 120 extends from the proximal end 54 of the shield 22 to the distal end 52 thereof, and is sized and shaped so as to slidably receive "TAB 1" (see FIG. 8). A lower lock groove 122 and an upper lock groove 124 are formed on an opposite side of the raised segment 104. Both the lower lock groove 122 and the upper lock groove 124 extend from the proximal end 54 of the shield 22 to the distal end 52 thereof, and are sized and shaped so as to slidably receive "TAB 1" (see FIG. 8).

Figure 8:
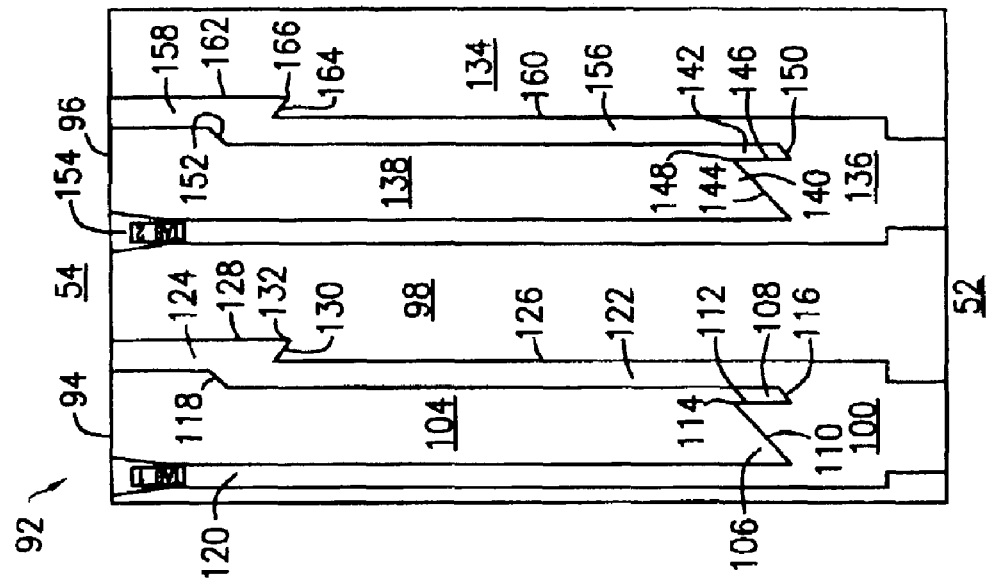
FIGS. 8–16 are sequential views similar to the view shown in FIG. 7, schematically illustrating ring tabs of the adaptor assembly of FIG. 2 in various positions along the interior of the shield illustrated in FIG. 7.

The elevated segment 98 includes a linearly extending wall 126 formed adjacent one side of the raised segment 104. Another linearly extending wall 128 is located proximal to the wall 126. More particularly, the wall 128 is spaced further from the raised segment 104 than the wall 126. The elevated segment 98 also includes an intermediate lock ramp 130 extending between the walls 126, 128 so as to form a V-shaped notch 132. As illustrated in FIG. 8, the V-shaped notch 132 is sized and shaped so as to be engageable by "TAB 1" (see FIG. 8).

The second set 96 includes an elevated segment 134 and an open area 136, each of which extends along the longitudinal axis 102 and is circumferentially spaced from the other. The open area 136 includes a raised segment 138 having a distal edge in the form of ratchet teeth 140, 142. More particularly, the tooth 140 has an inclined edge 144 which functions as a ramp so as to allow "TAB 2" (see FIG. 9) to slide therealong. The other tooth 142 has an axially extending linear edge 146 which functions as a stop, positioned adjacent to the inclined edge 144 so as to form a V-shaped trough 148 between the ratchet teeth 140, 142. The V-shaped trough 148 is sized and shaped so as to temporarily lock "TAB 2" (see FIG. 10) of the ring 30 therein as will be explained in further detail hereinafter.

Both the inclined edge 144 and the linear edge 146 of the ratchet teeth 140, 142 protrude into the open area 136 and are located adjacent to the distal end 52 of the shield 22. The tooth 142 also includes a lower lock ramp 150 which functions as a guide and which is positioned adjacent the linear edge 146 of the ratchet tooth 142. The raised segment 138 has a proximal edge in the form of an upper lock ramp 152.

A linearly extending assembly groove 154 is formed on one side of the raised segment 138. The assembly groove 154 extends from the proximal end 54 of the shield 22 to the distal end 52 thereof, and is sized and shaped so as to slidably receive "TAB 2" (see FIG. 8). A lower lock groove 156 and an upper lock groove 158 are formed on an opposite side of the raised segment 138. Both the lower lock groove 156 and the upper lock groove 158 extend from the proximal end 54 of the shield 22 to the distal end 52 thereof, and are sized and shaped so as to slidably receive "TAB 2" (see FIG. 8).

The elevated segment 134 includes a linearly extending wall 160 formed adjacent one side of the raised segment 138. Another linearly extending wall 162 is located proximal to the wall 160. More particularly, the wall 162 is spaced further from the raised segment 138 than the wall 160. The elevated segment 134 also includes an intermediate lock ramp 164 extending between the walls 160, 162 so as to form a V-shaped notch 166. As illustrated in FIG. 8, the V-shaped notch 166 is sized and shaped so as to be engageable by "TAB 2" (see FIG. 8).

The following description will describe the affixation of the parts of the adaptor assembly 20 (i.e., the shield 22, the spring 24, the retaining bushing 26, the adaptor hub 28, and the ring 30) to the barrel 12 and the needle assembly 16. Initially, the ring 30 is mounted onto the adaptor hub 28 such that the ring 30 is captured between the projections 66 and the retention bead 84. The proximal end 68 (see FIG. 2) of the adaptor hub 28 is then affixed to the mounting surface 36 (i.e., the distal end 38) of the barrel 12 (see FIG. 1). The spring 24 is mounted within the shield 22, and the retaining bushing 26 is affixed to the barrel 12. Lastly, the shield 22 is placed over the needle assembly 16 such that the proximal end 54 of the shield 22 is adjacent to the mounting surface 36 (i.e., the distal end 38) of the barrel 12.

In operation, the barrel 12 is initially in its retracted position (see FIG. 4) and the spring 24 is initially substantially fully extended. "TAB 1" is positioned in the V-shaped trough 76 of the adaptor hub 28 (see FIG. 2). The safety syringe 10 is delivered to a user in this position. FIG. 8 shows "TAB 1" initially positioned in the assembly groove 120 at the proximal end 54 of the shield 22. For simplicity, the operation of only "TAB 1" is described below. It will be understood that "TAB 2" operates in the same manner as that of "TAB 1".

Figure 9:
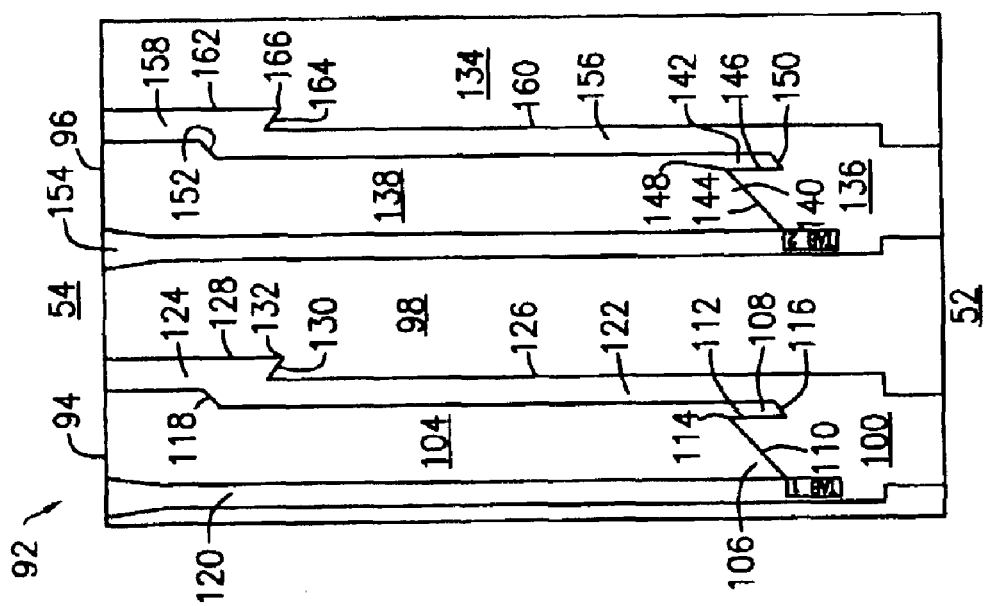

Referring now to FIG. 9, the barrel 12 is displaced toward its extended position (see FIG. 5) as the plunger 18 is pushed axially toward the distal end 52 of the shield 22. As the barrel 12 moves toward its extended position, the spring 24 compresses and, the ring 30 and the adaptor hub 28 (see FIG. 2) move toward the distal end 52 of the shield 22 such that the first inclined ramp 72 of the adaptor hub 28 and "TAB 1" are aligned with the inclined edge 110 of the ratchet tooth 106.

Figure 10:
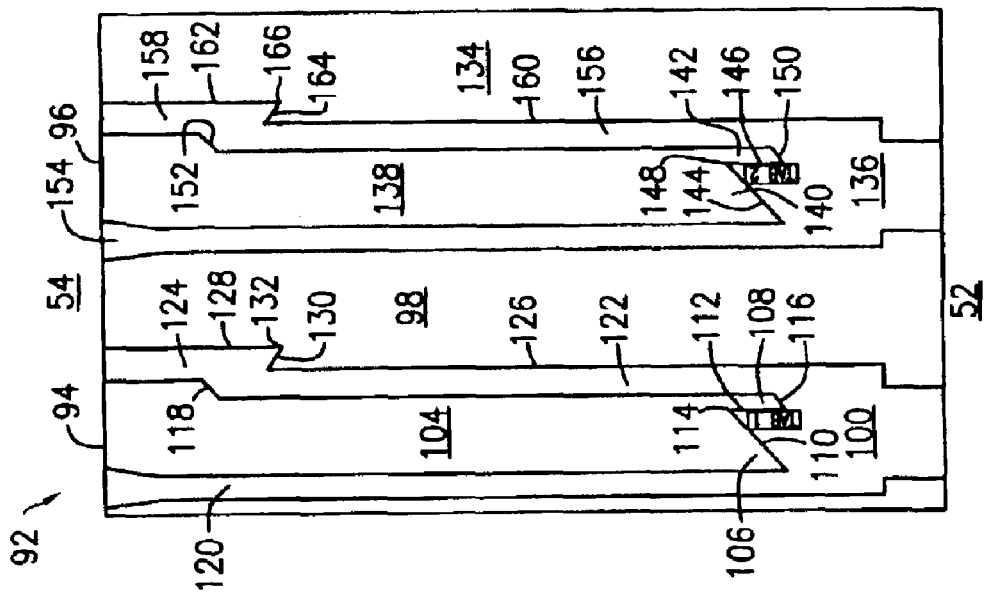

Still referring to FIG. 9, upon release of the plunger 18, the spring 24 urges the barrel 12 toward the proximal end 54 of the shield 22, thereby moving the ring 30 and the adaptor hub 28 (see FIG. 2) in the same direction such that "TAB 1" contacts and slides along the inclined edge 110 of the ratchet tooth 106 until it engages the linear edge 112 of the ratchet tooth 108, thereby rotating the ring 30 to a position illustrated in FIG. 10. In the position illustrated in FIG. 10, "TAB 1" is temporarily locked in the V-shaped trough 114 of the raised segment 104 such that it cannot rotate any further, thereby ceasing the rotation of the ring 30 and temporarily locking the barrel 12 in place. Once the barrel 12 is temporarily locked in place, the safety syringe 10 is ready for use.

To use the safety syringe 10, the needle 42 is first exposed by removing the cover 44 (see FIG. 1) therefrom. Then, the plunger 18 is used to place the desired fluid in the cavity 14 (see FIG. 1) of the barrel 12 by withdrawing the plunger 18 in a direction away from the shield 22 so as to create a vacuum in the cavity 14 as is known in the art. The plunger 18 is then depressed to inject the fluid in a conventional manner.

After use, the safety syringe 10 can be locked in a safety position, in which position the needle 42 is permanently locked inside the shield 22 so as to prevent needle pricks. To place the safety syringe 10 in the safety position, the plunger 18 is depressed to thereby urge the barrel 12 toward the distal end 52, thereby moving the ring 30 and the adaptor hub 28 in the same direction such that "TAB 1" moves adjacent to the lower lock ramp 116 as illustrated in FIG. 11.

Figure 11:
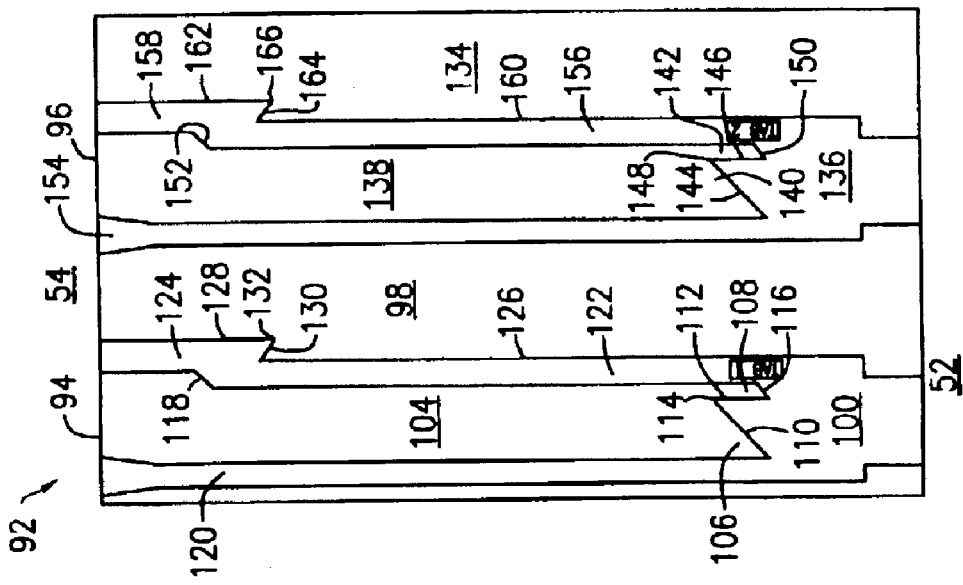
Figure 12:
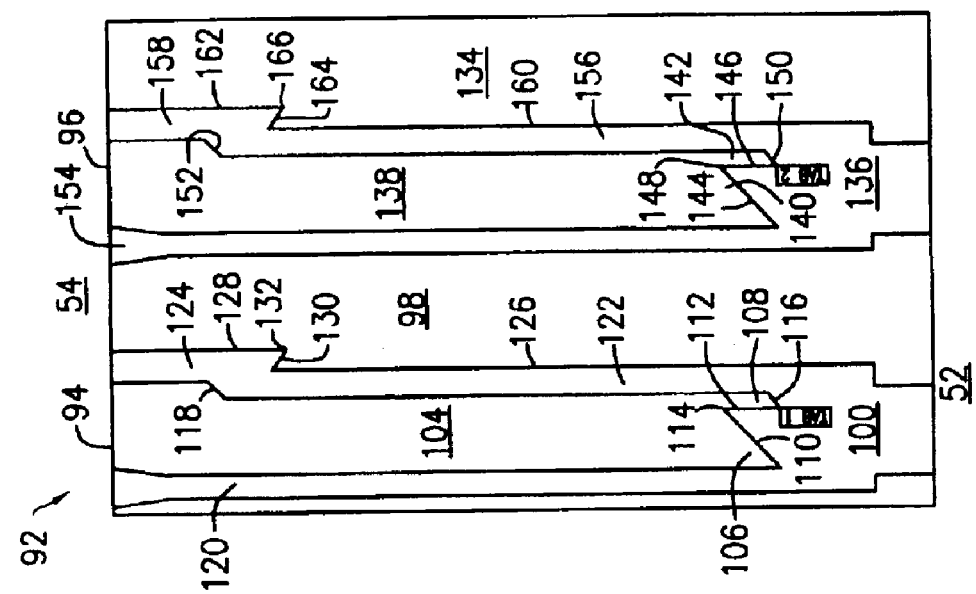
Figure 13:
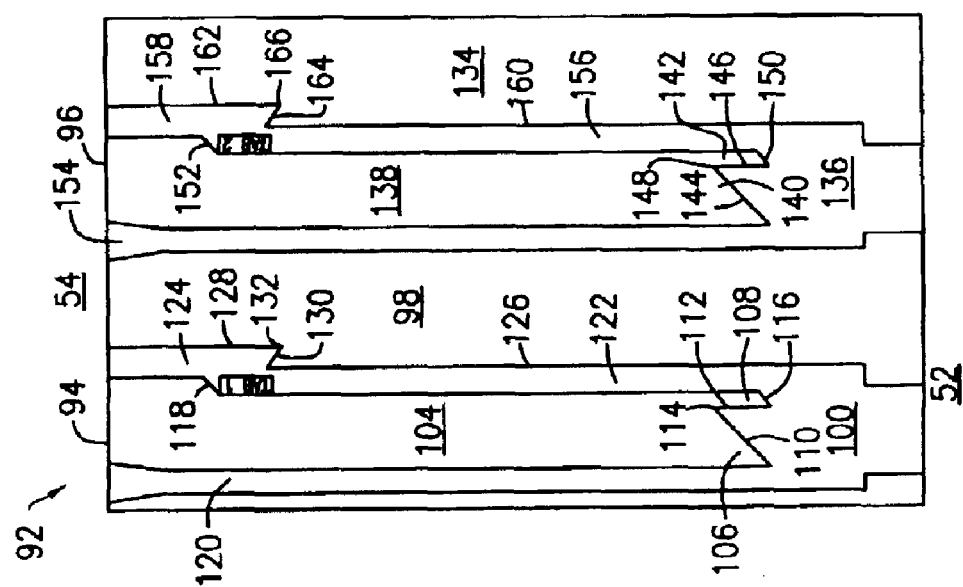

Still referring to FIG. 11, upon release of the plunger 18, the spring 24 urges the barrel 12 toward the proximal end 54, thereby moving the ring 30 and the adaptor hub 28 in the same direction such that "TAB 1" contacts and slides along the second inclined ramp 78 of the adaptor hub 28 (see FIG. 2). As the "TAB 1" slides along the second inclined ramp 78, the ring 30 rotates to a position illustrated in FIG. 12. When "TAB 1" contacts the wall 126, the ring 30 ceases to rotate relative to the shield 22 and is axially aligned with the lower lock groove 122. The spring 24 urges the barrel 12 to its retracted position (see FIG. 4), thereby moving the ring 30 and the adaptor hub 28 toward the proximal end 54 such that "TAB 1" traverses the lower lock groove 122 until it contacts the upper lock ramp 118 of the raised segment 104 as illustrated in FIG. 13.

Figure 14:
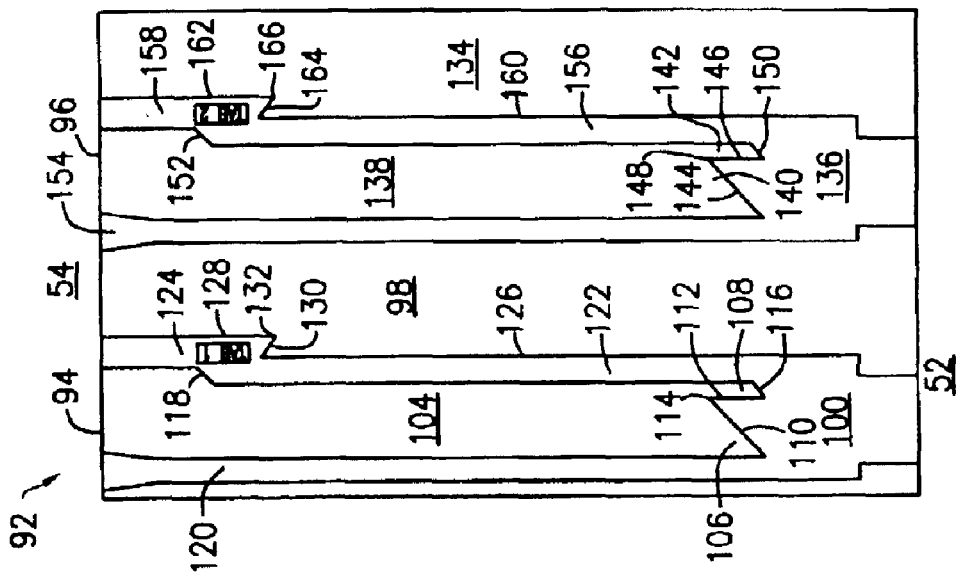
Figure 15:
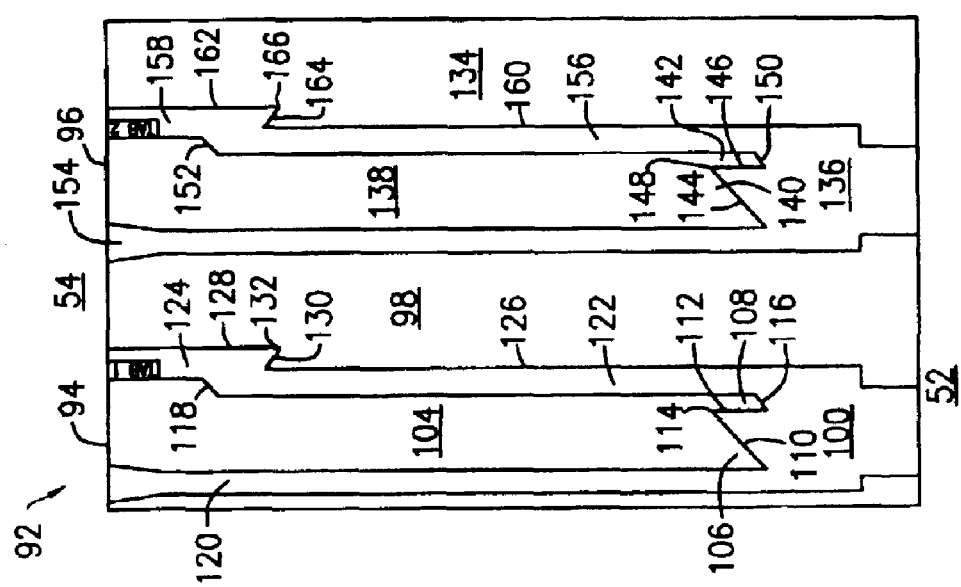

The force of the spring 24 causes the ring 30 and the adaptor hub 28 to move toward the proximal end 54 of the shield 22 such that "TAB 1" slides along the upper lock ramp 118, rotating the ring 30 to a position illustrated in FIG. 14. Referring now to FIG. 15, the force of the spring 24 continues to move the ring 30 and the adaptor hub 28 toward the proximal end 54 such that "TAB 1" is finally adjacent to the proximal end 54. This places the safety syringe 10 in the safety position, in which it can be disposed of in a normal manner.

Figure 16:
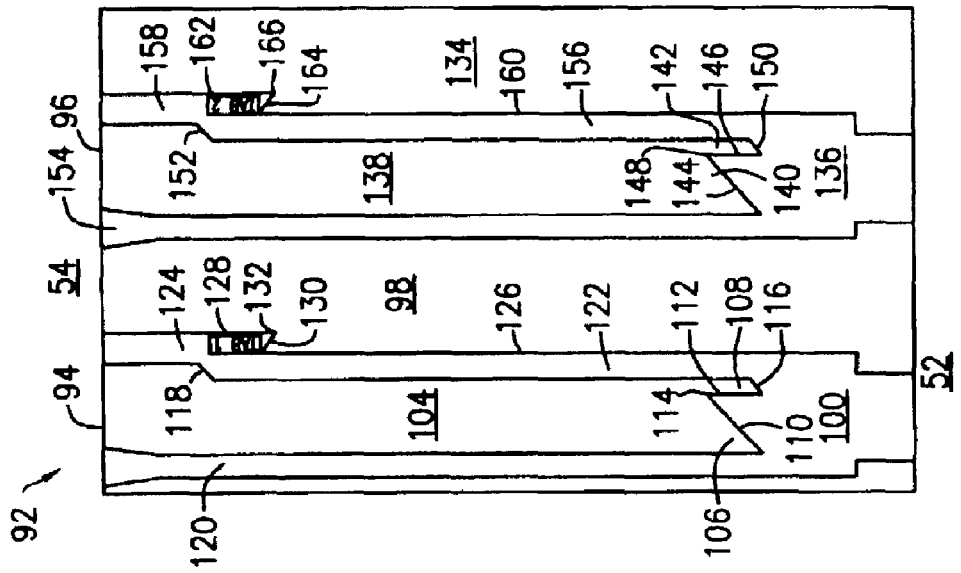

Referring now to FIG. 16, if the user attempts to reuse the safety syringe 10 by depressing the plunger 18, the barrel 12 will move toward the distal end 52, thereby moving the ring 30 and the adaptor hub 28 in the same direction such that "TAB 1" engages the V-shaped notch 132. The V-shaped notch 132 is sized and shaped such that it precludes lateral movement of "TAB 1", thereby permanently locking the barrel 12 in its retracted position such that the needle 42 is permanently concealed in the shield 22.

It should be appreciated that the present invention provides numerous advantages. For instance, the adaptor assembly 20 requires only a minimal number of parts in order to convert a conventional non-safety syringe into the safety syringe 10. The components of the adaptor assembly 20 (i.e., the shield 22, the spring 24, the retaining bushing 26, the adaptor hub 28, and the ring 30) can be marketed as a combination or can be individually sold. It is noted that the safety syringe 10 can be marketed with the components of the adaptor assembly 20 pre-assembled to the barrel 12. The adaptor assembly 20 is relatively inexpensive to manufacture. Because users typically have a supply of conventional syringes in stock, it costs less to convert the existing conventional non-safety syringes into safety syringes than to purchase new safety syringes. The safety syringe 10 is sized and shaped so as to allow for only a single use thereof, and includes a safety feature so as to prevent needle pricks.

The adaptor assembly 20 can have numerous modifications and variations. For example, although the ring 30, the adaptor hub 28, and the retaining bushing 26 are molded of polypropylene, other materials can be used besides polypropylene. Although two tabs 88 on the ring 30 are shown, the number of tabs 88 can vary. Although four locking barbs 80 are shown, the number of barbs 80 can vary. The adaptor assembly 20 can be employed with conventional non-safety syringes that do not include the plunger 18. If the plunger 18 is not included, the barrel 12 can be placed in the extended position (see FIG. 5) by pushing the flange 32 of the barrel 12 axially toward the shield 22. The lower lock ramp 116 of the tooth 108 can be eliminated and replaced with a linear edge (not shown).

It will be understood that the embodiment described herein is merely exemplary and that a person skilled in the art may make many variations and modifications without departing from the spirit and scope of the invention. All such variations and modifications, including those discussed above, are intended to be included within the scope of the invention as defined in the appended claims.

The invention claimed is:

1. A safety syringe, comprising a shield having a bore which extends from a distal end of said shield to a proximal end of said shield, said shield including an interior wall; a barrel having a distal end located in said shield and a proximal end located externally of said shield, said barrel being mounted for reciprocating movement within said shield such that said barrel is movable between a retracted position, in which said distal end of said barrel is located proximate said proximal end of said shield, and an extended position, in which said distal end of said barrel is located proximate said distal end of said shield; a needle assembly attached to said barrel at said distal end thereof, said needle assembly having a needle which extends in a direction away from said distal end of said barrel; a hub sized and shaped so as to be attached to said distal end of said barrel; urging means for automatically urging said barrel into its said retracted position from its said extended position; and a ring rotatably mounted on said hub such that said ring is rotatable relative to said shield, said interior wall of said shield including means for locking said barrel in its said retracted position, said ring including at least one tab sized and shaped so as to engage said locking means of said shield when said barrel is in its said retracted position, whereby said barrel is prevented from being moved back to its said extended position.

2. The safety syringe of claim 1, wherein said hub is sized and shaped so as to be retrofitted on said distal end of said barrel.

3. The safety syringe of claim 2, wherein said hub includes a cylindrical wall and an interior hollow defined by said cylindrical wall, said cylindrical wall having a first diameter, said distal end of said barrel having a second diameter, said first diameter of said cylindrical wall being larger than said second diameter of said distal end of said barrel so as to allow said cylindrical wall to be received onto said distal end of said barrel.

4. The safety syringe of claim 3, wherein said hub includes at least one projection having a first ramp which is sized and shaped so as to allow said at least one tab to slide therealong.

5. The safety syringe of claim 4, wherein said at least one projection of said hub further includes a first stop positioned adjacent said first ramp.

6. The safety syringe of claim 5, wherein said at least one projection of said hub further includes a second ramp which is sized and shaped so as to allow said at least one tab to slide therealong.

7. The safety syringe of claim 6, wherein said hub further includes retaining means for retaining said hub on said distal end of said barrel.

8. The safety syringe of claim 7, wherein said retaining means includes a plurality of barbs, each of said barbs projecting into said interior hollow of said hub from said cylindrical wall thereof.

9. The safety syringe of claim 8, wherein each of said barbs includes an edge which is deformed outwardly relative to said cylindrical wall of said hub.

10. The safety syringe of claim 8, wherein said hub further includes a retention bead positioned on said cylindrical wall, said retention bead sized and shaped so as to retain said ring on said hub.

11. The safety syringe of claim 10, wherein said urging means is a compression spring mounted within said bore of said shield.

12. The safety syringe of claim 11, further including a plunger mounted for reciprocating movement within said barrel so as to move said barrel to its said extended position.

13. The safety syringe of claim 12, wherein said locking means includes a V-shaped notch which is sized and shaped so as to preclude lateral movement of said at least one tab.

14. The safety syringe of claim 13, wherein said interior wall of said shield includes an elevated segment and an open area circumferentially spaced from said elevated segment, said open area including a raised segment having a third ramp sized and shaped so as to allow said at least one tab to slide therealong and a second stop positioned adjacent said third ramp.

15. The safety syringe of claim 14, wherein said raised segment is sized and shaped so as to form a first groove on one side thereof and a second groove on an opposite side thereof, said first groove extending from said proximal end of said shield to said distal end of said shield and being sized and shaped so as to slidably receive said at least one tab, said second groove extending from said proximal end of said shield to said distal end of said shield and being sized and shaped so as to slidably receive said at least one tab, said elevated segment extending from said proximal end of said shield to said distal end of said shield.

16. The safety syringe of claim 15, wherein said raised segment includes guiding means for guiding said at least one tab into said second groove.

17. In a syringe which includes a barrel with a distal end and a needle assembly releaseably secured to said barrel, the improvement wherein said syringe is retrofitted with an adaptor assembly for converting said syringe into a safety syringe, said adaptor assembly comprising a shield having a bore which extends from a distal end of said shield to a proximal end of said shield, said shield including an interior wall, said shield cooperating with said barrel of said syringe such that said barrel is movably mounted in said bore of said shield so as to be movable between a retracted position, in which said distal end of said barrel is located proximate said proximal end of said shield, and an extended position, in which said distal end of said barrel is located proximate said distal end of said shield; a hub sized and shaped so as to be attached to said distal end of said barrel, said hub including a projection for engagement with said shield; urging means for automatically urging said barrel into its said retracted position from its said extended position; and a ring rotatably mounted on said hub such that said ring is rotatable relative to said shield, said interior wall of said shield including means for locking said barrel, said ring including at least one tab sized and shaped so as to engage said locking means of said shield when said barrel is in its said retracted position, whereby said barrel is prevented from being moved back to its said extended position.

18. An adaptor assembly affixable to a non-safety syringe having a barrel with a distal end and a needle assembly releaseably secured to the barrel, said adaptor assembly comprising a shield having a bore which extends from a distal end of said shield to a proximal end of said shield, said shield including an interior wall, said shield cooperating with the barrel of the non-safety syringe such that the barrel is movable between a retracted position, in which the distal end of the barrel is located proximate said proximal end of said shield, and an extended position, in which the distal end of the barrel is located proximate said distal end of said shield; a hub sized and shaped so as to be retrofitted to the distal end of the barrel, said hub including a projection for engagement with said shield; and a ring rotatably mounted on said hub such that said ring is rotatable relative to said shield, said interior wall of said shield including means for locking said barrel, said ring including a tab sized and shaped so as to engage said locking means of said shield when the barrel is in its retracted position.

19. The safety syringe of claim 18, further comprising a compression spring mounted within said bore of said shield, said compression spring sized and shaped so as to automatically urge the barrel into its retracted position.

20. A method for converting a non-safety syringe into a safety syringe, said method comprising the steps of:

(a) providing a non-safety syringe which includes a barrel having a distal end and a needle assembly extending in a direction away from the distal end of the barrel;

(b) providing an adaptor assembly which includes a shield having a bore which extends from a distal end of the shield to a proximal end of the shield, a hub sized and shaped so as to be attached to the distal end of the barrel, a ring sized and shaped so as to be rotatably mounted on the hub, and urging means sized and shaped to be mounted in the bore of the shield;

(c) mounting the ring onto the hub;

(d) affixing the hub to the distal end of the barrel;

(e) mounting the urging means within the shield; and (f) placing the proximal end of the shield over the needle assembly.

* * * * *